(12) United States Patent
Heep et al.

(10) Patent No.: US 9,095,511 B2
(45) Date of Patent: Aug. 4, 2015

(54) STABILIZATION OF OILY SUSPENSIONS COMPRISING HYDROPHOBIC SILICAS

(75) Inventors: Iris Heep, Cologne (DE); Hans-Juergen Hamann, Dormagen (DE); Sabine Koelling, Leverkusen (DE); Gert Daube, Engelskirchen (DE); Klaus-Juergen Steffens, Rheinbach (DE); Rolf Daniels, Salzgitter (DE)

(73) Assignee: Bayer Intellectual Property GmbH (DE)

( * ) Notice: Subject to any disclaimer, the term of this patent is extended or adjusted under 35 U.S.C. 154(b) by 372 days.

(21) Appl. No.: 12/739,873

(22) PCT Filed: Nov. 12, 2008

(86) PCT No.: PCT/EP2008/009526
§ 371 (c)(1),
(2), (4) Date: Apr. 26, 2010

(87) PCT Pub. No.: WO2009/065514
PCT Pub. Date: May 28, 2009

(65) Prior Publication Data
US 2010/0261688 A1    Oct. 14, 2010

(30) Foreign Application Priority Data
Nov. 19, 2007    (DE) .......................... 10 2007 055 341

(51) Int. Cl.
| | | |
|---|---|---|
| *A61K 9/10* | (2006.01) | |
| *A61K 31/44* | (2006.01) | |
| *A61K 31/47* | (2006.01) | |
| *A61K 31/545* | (2006.01) | |
| *A61K 31/7034* | (2006.01) | |
| *A61K 47/10* | (2006.01) | |
| *A61K 47/44* | (2006.01) | |
| *A61K 47/12* | (2006.01) | |
| *A61K 47/26* | (2006.01) | |
| *A61K 45/06* | (2006.01) | |
| *A61K 31/53* | (2006.01) | |
| *A61K 47/02* | (2006.01) | |
| *A61K 47/14* | (2006.01) | |

(52) U.S. Cl.
CPC . *A61K 9/10* (2013.01); *A61K 31/44* (2013.01); *A61K 31/47* (2013.01); *A61K 31/53* (2013.01); *A61K 31/545* (2013.01); *A61K 31/7034* (2013.01); *A61K 45/06* (2013.01); *A61K 47/02* (2013.01); *A61K 47/10* (2013.01); *A61K 47/12* (2013.01); *A61K 47/14* (2013.01); *A61K 47/26* (2013.01); *A61K 47/44* (2013.01)

(58) Field of Classification Search
CPC ......... A61K 9/10; A61K 31/44; A61K 47/44; A61K 47/26; A61K 47/14; A61K 47/12; A61K 47/10; A61K 47/02; A61K 45/06; A61K 31/7034; A61K 31/545; A61K 31/47; A61K 31/53; A61K 2300/00
USPC .......... 424/400; 514/171, 253.08, 300, 229.2, 514/241
See application file for complete search history.

(56) References Cited

U.S. PATENT DOCUMENTS

| | | | |
|---|---|---|---|
| 4,079,131 A | 3/1978 | Lin et al. | |
| 4,382,892 A | 5/1983 | Hayakawa et al. | |
| 4,472,405 A | 9/1984 | Stern | |
| 4,670,444 A | 6/1987 | Grohe et al. | |
| 4,704,459 A | 11/1987 | Todo et al. | |
| 4,730,000 A | 3/1988 | Chu | |
| 4,861,779 A | 8/1989 | Jefson et al. | |
| 5,858,330 A | 1/1999 | Boltri et al. | |
| 6,278,013 B1 | 8/2001 | Bartel et al. | |
| 6,528,539 B1 | 3/2003 | Abramovici et al. | |
| 6,602,490 B1 * | 8/2003 | Cloonan | 424/49 |
| 2001/0006671 A1 | 7/2001 | Goodman et al. | |
| 2003/0039668 A1 * | 2/2003 | Gulla et al. | 424/401 |
| 2005/0142225 A1 | 6/2005 | Kysilka et al. | |
| 2007/0082911 A1 | 4/2007 | Daube et al. | |
| 2009/0011045 A1 * | 1/2009 | Mertin et al. | 424/618 |
| 2009/0239835 A1 * | 9/2009 | Daube et al. | 514/179 |

FOREIGN PATENT DOCUMENTS

| | | |
|---|---|---|
| CA | 2369594 A1 | 11/2000 |
| CA | 2552909 A1 | 7/2005 |
| EP | 0213552 A2 | 11/1987 |
| EP | 0 310 801 * | 4/1989 |
| EP | 0310801 A1 | 4/1989 |
| JP | H01-156911 A | 6/1989 |
| JP | 4077421 | 3/1992 |
| JP | 6256176 | 9/1994 |
| JP | 3446309 B2 * | 1/1996 |
| WO | 03002254 | 1/2003 |
| WO | 03063877 | 8/2003 |
| WO | 2005025566 | 3/2005 |
| WO | 2005065713 A2 | 7/2005 |
| WO | 2006008640 | 1/2006 |
| WO | WO 2006061155 * | 6/2006 |
| WO | WO 2006061156 * | 6/2006 |

OTHER PUBLICATIONS

Machine Translation of JP 3446309B (Eng.), 1996.*

(Continued)

*Primary Examiner* — Blessing M Fubara
(74) *Attorney, Agent, or Firm* — Senniger Powers LLP

(57) ABSTRACT

The invention relates to a stabilization of fluid oil-based suspensions comprising a hydrophobic silica, and medicaments based on such suspensions.

14 Claims, 1 Drawing Sheet

(56) References Cited

OTHER PUBLICATIONS

Lippold et al., Dermatopharmazie; Wissenschaftliche Verlagsgesellschaft MBH Stuttgart, (2001), pp. 105-138, Ch. 6.
Date Restricted Google Search (Jan. 1, 2000 to May 23, 2004) for "Aurizon Ear Drops", printed Jan. 17, 2011, 1 page.
Aurizon Ear Drops, Suspension, "Summary of Product Characteristics," Jan. 2006, Vetoquinol UK Limited, 4 pages.
Date Restricted Google Search (Jan. 1, 2000 to Nov. 19, 2007) for "Sorbitan Oleate Stabilizer", printed Jan. 17, 2011, 2 pages.
Safety (MSDS) Data for Sorbitan Monooleate, updated Oct. 10, 2003, Oxford University, printed Jan. 17, 2011, http://msds.chem.ox.ac.uk/SO/sorbitan_monooleate.html, 2 pages.

* cited by examiner

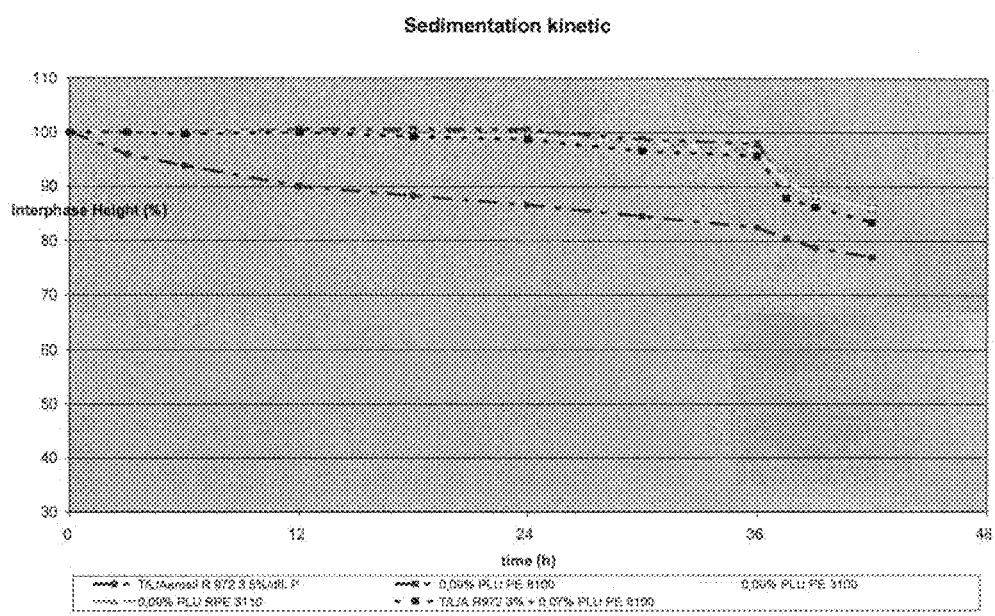

STABILIZATION OF OILY SUSPENSIONS COMPRISING HYDROPHOBIC SILICAS

The invention relates to a stabilization of fluid oil-based suspensions comprising a hydrophobic silica, and medicaments based on such suspensions.

Formulation of a medicament based on oils may have various advantages, e.g. in the tolerability for the patient or in the stability of the active ingredient. However, oils which can be used pharmaceutically do not always have the necessary viscosity in order for example to reduce or avoid sedimentation of active ingredients. Thus, although most known substances used for increasing the viscosity of oils can be employed in cosmetics, they cannot be employed in pharmacy. Thus, for example, colloidal silicas are used to thicken oils for medicaments (US 2001-0006671, U.S. Pat. No. 4,079,131, WO 03-063877).

In WO 2006/008640, non-ionic emulsifiers are added to colloidal silicon dioxide (a hydrophilic silica) so that the active ingredient is wetted better in oils.

In WO 03/02254, colloidal silica, hydrophilic and hydrophobic silicas are mixed with hydrophilic polymers such as, for example, polyethylene glycol 200 or polyvinyl alcohol in oils. Interaction of the silica with the polymer is intended to reduce the use of the silica, raise the yield point and lower the viscosity on shearing.

FR 2790200 likewise mentions hydrophobic silicas, but explicitly specifically without the addition of stabilizers.

WO 2006/061155 and WO 2006/061156 describe not only hydrophilic but also hydrophobic silicas in oils. Substances which can generally be used in this connection are also for example non-ionic surfactants or else for example polyethylene glycol 200.

Hydrophilic silicas have the disadvantage in oily formulations that they are very sensitive to water or moisture and adsorb moisture even from the ambient air. As a result, the viscosity of the formulation increases and, for example, the removability from the primary packaging is no longer possible to the indicated extent. This is unacceptable in particular for medicaments. If, for example, single-dose containers made of plastics are used for these formulations, the effect of the sensitivity to moisture is particularly evident, because plastic containers are not moisture-tight, and the formulation in the filled container attracts moisture and the viscosity may increase. In addition, the ratio of the surface area of the formulation to the surrounding air in single-dose containers is particularly unfavorable by comparison with multidose containers.

This sensitivity to moisture can be overcome by using hydrophobic silicas for stabilizing suspensions against sedimentation. A distinct disadvantage of hydrophobic silicas is, however, that the long-term stability in relation to sedimentation stabilization is lower than that of hydrophilic silicas. The lower long-term stability is characterized in that the original viscosity of the oily formulations decreases over the course of weeks or months, which is unacceptable for medicaments since this may lead for example to unwanted sedimentations.

It has surprisingly been found that the long-term stability of oily formulations with hydrophobic silicas can be distinctly improved by adding amphiphilic compounds. This effect scarcely occurs on use of hydrophilic silicas. This effect has not yet been described in the state of the art for oily suspensions which specifically comprise hydrophobic silicas.

The Invention Therefore Relates to:

The use of amphiphilic substances for stabilizing fluid oil-based suspensions comprising a hydrophobic silica.

Such fluid suspensions are preferably used in formulations for medicaments.

The Invention Therefore Relates Further to:

Medicaments comprising in an oily base:
a) an active ingredient
b) a hydrophobic silica
c) a polyoxyethylated compound "Oil-based" means that the corresponding suspension or the corresponding medicament comprises an oily base. It is possible to use as oily base natural (animal or vegetable), synthetic and semisynthetic oils or fats. Examples thereof are soybean, sunflower, cottonseed, olive, peanut, safflower, palm, rapeseed, coconut, corn or castor oil. Preferably used are medium-chain triglycerides (triglycerides with saturated fatty acids, preferably octanoic and decanoic acid), propylene glycol diesters of caprylic/capric acid, low-viscosity paraffin or sesame oil; of these, the medium-chain triglycerides and propylene glycol diesters of caprylic/capric acid are particularly preferably used.

The oily base is typically employed in a proportion of 99-72% by weight, preferably of 99-88% by weight, particularly preferably of 97-92% by weight, based on the relevant suspension or the finished medicament.

The suspensions may have different viscosities, so that in principle a range from low-viscosity suspensions to pastes is conceivable. Preference is given to fluid systems which include low-viscosity and also higher-viscosity systems as long as they still flow under their own weight. Preferred fluid systems have a yield point, i.e. these systems flow after shearing (e.g. by shaking). In many cases, the active ingredients do not dissolve sufficiently, or at all, in the fluid base, so that the active ingredient must also be suspended. For this reason, hydrophobic silicas are employed as thickeners for stabilizing the suspension against sedimentation.

Hydrophobic silicas are silicas which are not wetted by water; this means that they float on the water surface. Likewise suitable are hydrophobicized mixed oxides of silicon dioxide and aluminum oxide, but hydrophobic pure silicas are preferred. They are produced by mixing hydrophilic silica with silanes (halosilanes, alkoxysilanes, silazanes, siloxanes). This entails silanol groups being alkylated by alkyl groups preferably having up to 18 carbon atoms, particularly preferably having up to 8 carbon atoms, very particularly preferably having up to 4 carbon atoms, especially by methyl groups. Examples of silanes used in the production of hexamethyldisilazane or, preferably, dimethyldichlorosilane. The appropriate hydrophobic silicas may be derived from precipitated, colloidal, precompacted or pyrogenic silicas, with preference for pyrogenic silicas. For example, reaction of a hydrophilic silica with dimethyldichlorosilane results in hydrophobic Aerosil having the proprietary name Aerosil® R 972; this has a degree of methylation of 66%-75% (determined by titration of the remaining silanol groups).

The hydrophobic silica is employed in the formulations typically in a proportion of 0.1-10% by weight, preferably employed with 0.5-5% by weight, particularly preferably with 1.5-4.0% by weight.

Amphiphilic compounds consist of a polar (hydrophilic) and an apolar (hydrophobic) part. Typical amphiphiles are fatty acids, surfactants and phospholipids. Active ingredients may also be amphiphilic in nature. Thus, for example, quinolones or else fluoroquinolones are amphiphilic. The molecules have an acid group and a basic group. The acid group may be in deprotonated form and then has a negative charge; the basic group may be in protonated form and then has a positive charge. Each charged part of the molecule is highly polar and hydrophilic, while the remainder of the molecule is less polar and thus more hydrophobic.

In the context of this invention, preferred amphiphilic compounds are polyoxyethylated compounds. Polyoxyethylated compounds, also referred to as polyethoxylated compounds, are prepared for example by reaction with ethylene oxide. They have one or more concatenated units of the formula —[O—CH$_2$—CH$_2$]—. Polyoxyethylated compounds which may be mentioned in particular are:

Nonionic amphiphilic polyoxyethylated compounds such as
- poloxamers, preferably with molar masses of from 100 to 5000 g/mol, particularly preferably with molar masses of from 1000 to 3500 g/mol. Poloxamer is the international non-proprietary name for block copolymers of ethylene oxide and methyloxirane,
- polyoxyethylene fatty acid glycerides, also called nonionic emulsifiers, preferably for example glycerol polyethylene glycol ricinoleate,
- polyoxyethylene sorbitan fatty acid esters, preferably for example polyoxyethylene 20 sorbitan monooleate,
- polyoxyethylene fatty acids such as macrogol 15 hydroxystearate (=Solutol HS15, obtainable by reacting 15 mol of ethylene oxide and 1 mol of 12-hydroxystearic acid)
- polyoxyethylene fatty alcohols such as hydroxypolyethoxydodecane.

Fatty acid or fatty alcohol stands in particular for the corresponding compounds having at least 6 carbon atoms and normally not more than 30 carbon atoms.

The amphiphilic, especially the polyoxyethylated, compound is typically employed in the formulation in a proportion of 0.001-0.15% by weight, preferably with 0.005-0.09% by weight and particularly preferably with 0.005-0.08% by weight, especially 0.01-0.07% by weight.

The oil-based suspensions of the invention are preferably employed in medicaments. They then comprise one or more active pharmaceutical ingredients.

Examples which may be mentioned are anti-infective; these are in particular compounds having antibacterial activity, such as penicillins, cephalosporins, aminoglycosides, sulfonamides and, in particular, quinolones.

Quinolones, preferably fluoroquinolones, are inter alia compounds as disclosed in the following documents: U.S. Pat. No. 4,670,444 (Bayer AG), U.S. Pat. No. 4,472,405 (Riker Labs), U.S. Pat. No. 4,730,000 (Abbott), U.S. Pat. No. 4,861,779 (Pfizer), U.S. Pat. No. 4,382,892 (Daiichi), U.S. Pat. No. 4,704,459 (Toyama); specific examples of quinolones which may be mentioned are pipemidic acid and nalidixic acid; examples of fluoroquinolines which may be mentioned are: benofloxacin, binfloxacin, cinoxacin, ciprofloxacin, danofloxacin, difloxacin, enoxacin, enrofloxacin, fleroxacin, ibafloxacin, levofloxacin, lomefloxacin, marbofloxacin, moxifloxacin, norfloxacin, ofloxacin, orbifloxacin, pefloxacin, temafloxacin, tosufloxacin, sarafloxacin, sparfloxacin.

A preferred group of fluoroquinolones are those of the formula (I) or (II):

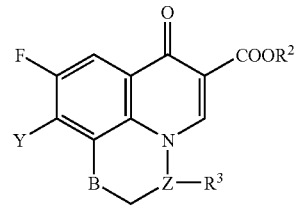

(I)

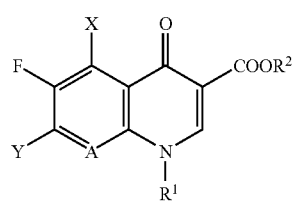

(II)

in which
X is hydrogen, halogen, C$_{1-4}$-alkyl, C$_{1-4}$-alkoxy, NH$_2$,
Y is radicals of the structures

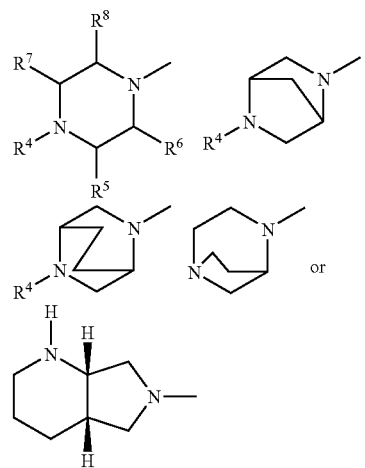

in which
R$^4$ is optionally hydroxy- or methoxy-substituted straight-chain or branched C$_{1-4}$-alkyl, cyclopropyl, acyl having 1 to 3 C atoms,
R$^5$ is hydrogen, methyl, phenyl, thienyl or pyridyl,
R$^6$ is hydrogen or C$_{1-4}$-alkyl,
R$^7$ is hydrogen or C$_{1-4}$-alkyl,
R$^8$ is hydrogen or C$_{1-4}$-alkyl,
and
R$^1$ is an alkyl radical having 1 to 3 carbon atoms, cyclopropyl, 2-fluoroethyl, methoxy, 4-fluorophenyl, 2,4-difluorophenyl or methylamino,
R$^2$ is hydrogen or optionally methoxy- or 2-methoxyethoxy-substituted alkyl having 1 to 6 carbon atoms, and cyclohexyl, benzyl, 2-oxopropyl, phenacyl, ethoxycarbonylmethyl, pivaloyloxymethyl,
R$^3$ is hydrogen, methyl or ethyl, and
A is nitrogen, =CH—, =C(halogen)-, =C(OCH$_3$)—, =C(CH$_3$)— or =C(CN),
B is oxygen, optionally methyl- or phenyl-substituted =NH or =CH$_2$,
Z is =CH— or =N—,
and the pharmaceutically usable salts and hydrates thereof.

The compounds of the formulae (I) and (II) may be in the form of their racemates or in enantiomeric forms.

Preference is given to compounds of the formula (I) in which
A is =CH— or =C—CN,
R$^1$ is optionally halogen-substituted C$_1$-C$_3$-alkyl or cyclopropyl,
R$^2$ is hydrogen or C$_{1-4}$-alkyl,
Y is radicals of the structures

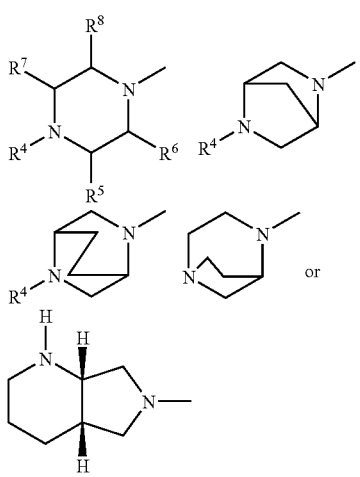

in which
R⁴ is optionally hydroxy-substituted straight-chain or branched $C_{1-3}$-alkyl, oxalkyl having 1 to 4 C atoms,
R⁵ is hydrogen, methyl or phenyl,
R⁷ is hydrogen or methyl,
R⁶ and R⁸ are hydrogen,
and the pharmaceutically usable hydrates and salts thereof.

Particular preference is given to compounds of the formula (I)
in which
A is =CH— or =C—CN,
R¹ is cyclopropyl,
R² is hydrogen, methyl or ethyl,
Y is radicals of the structures

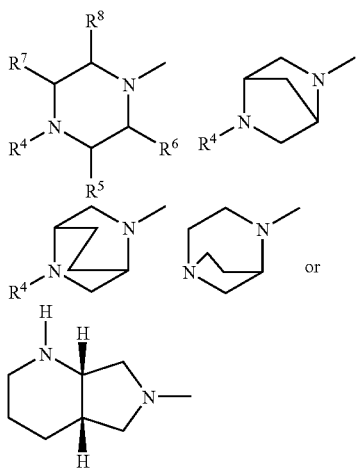

in which
R⁴ is methyl, optionally hydroxy-substituted ethyl,
R⁵ is hydrogen or methyl,
R⁷ is hydrogen or methyl,
R⁶ and R⁸ are hydrogen,
and the pharmaceutically usable salts and hydrates thereof.

Suitable salts are pharmaceutically usable acid addition salts and basic salts.

Pharmaceutically usable salts mean for example the salts of hydrochloric acid, sulfuric acid, acetic acid, glycolic acid, lactic acid, succinic acid, citric acid, tartaric acid, methanesulfonic acid, 4-toluenesulfonic acid, galacturonic acid, gluconic acid, embonic acid, glutamic acid or aspartic acid. The compounds of the invention can also be bound to acidic or basic ion exchangers. Pharmaceutically usable basic salts which may be mentioned are the alkali metal salts, for example the sodium or potassium salts, the alkaline earth metal salts, for example the magnesium or calcium salts; the zinc salts, the silver salts and the guanidinium salts.

Hydrates mean both the hydrates of the fluoroquinolones themselves and the hydrates of salts thereof.

Fluoroquinolones which may be mentioned as particularly preferred are the compounds described in WO 97/31001, in particular 8-cyano-1-cyclopropyl-7-((1S,6S)-2,8-diazabicyclo[4.3.0]nonan-8-yl)-6-fluoro-1,4-dihydro-4-oxo-3-quinolinecarboxylic acid (pradofloxacin) with the formula

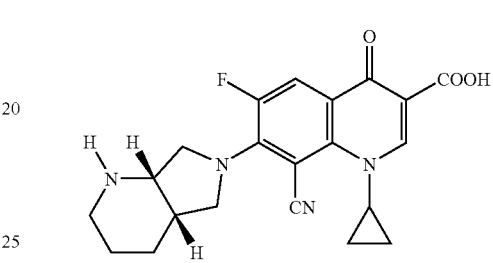

Pradofloxacin is preferably employed in the form of its trihydrate.

Also particularly preferably employed is enrofloxacin: 1-Cyclopropyl-7-(4-ethyl-1-piperazinyl)-6-fluoro-1,4-dihydro-4-oxo-3-quinolinecarboxylic acid

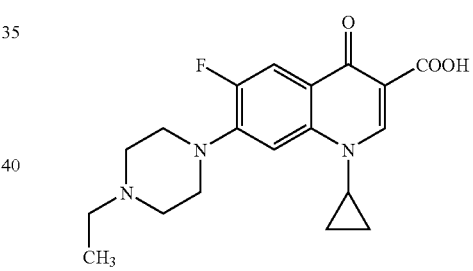

Besides enrofloxacin and pradofloxacin, further preferred quinolone anti-infectives which may be mentioned are marbofloxacin, orbifloxacin, difloxacin, ofloxacin and ibafloxacin.

Examples of penicillins are benzylpenicillin, ampicillin, amoxicillin, oxacillin, piperacillin, ticarcillin.

Examples of cephalosporins are cefalexin, cefadroxil, cefazolin, cefoxitin, ceftiofur.

Mention may be made for example of erythromycin, spiramycin, tylosin, tilmicosin as macrolide.

Sulfonamides which may be mentioned are for example trimethoprim and sulfadiazine (preferably employed in combination).

Aminoglycosides which may be mentioned are gentamycin, kanamycin, streptomycin, neomycin and spectinomycin.

A further antibiotic which may be mentioned is the lincosamide clindamycin.

Less preferred anti-infectives in the context of this invention are derived from silver, e.g. colloidal silver, silver nitrate or silver sulfadiazine. These may, however, be employed in combination with one of the anti-infectives described hereinabove and/or where appropriate a corticoid.

The anti-infective is typically employed in the proportion of 0.001-6% by weight, preferably 0.01-1.0% by weight, particularly preferably 0.1-0.8% by weight, based on the finished medicament.

Further active pharmaceutical ingredients which may be mentioned are antimycotics such as, for example, an imidazol or a triazol, ketokonazol, enilconazol, econazol, especially for example clotrimazol, miconazol or bifonazol.

The antimycotic is typically employed in a proportion of 0.01-10% by weight, preferably 0.1-5% by weight, particularly preferably 0.5-2% by weight, based on the finished medicament.

Further suitable active pharmaceutical ingredients are for example corticoids. Examples which may be mentioned are hydrocortisone, prednisolone, betamethasone, mometasone, clobetasone, flumethasone; preferably betamethasone, triamcinolone and in particular dexamethasone.

The corticoid is typically employed in a proportion of 0.001-2.0% by weight, preferably 0.005-0.5% by weight, particularly preferably 0.05-0.2% by weight, based on the finished medicament.

Further suitable active pharmaceutical ingredients are triazines, in particular the compounds of the formulae (I) or (II):

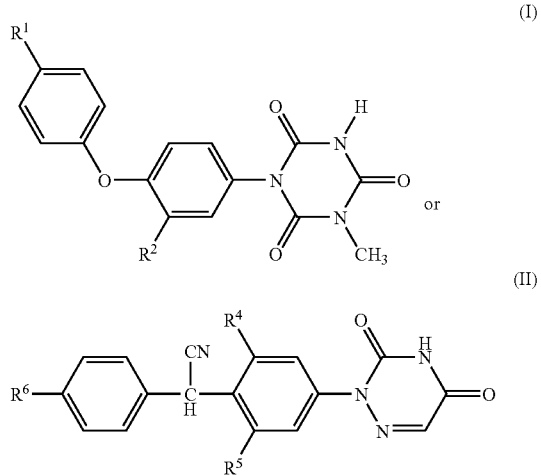

in which
$R^1$ is $R^3$—$SO_2$— or $R^3$—S—,
$R^2$ is alkyl, alkoxy, halogen or $SO_2N(CH_3)_2$, and
$R^3$ is haloalkyl,
$R^4$ and $R^5$ are independently of one another hydrogen or Cl, and
$R^6$ is fluorine or chlorine,
and the physiologically tolerated salts thereof.

The triazines are well known as active ingredients for coccidial infections per se, and mention may be made of the triazinetriones such as, for example, toltrazuril and ponazuril, and the triazinediones such as, for example, clazuril, diclazuril and letrazuril.

The triazinediones are represented by formula (II):
clazuril ($R^4$=Cl, $R^5$=H, $R^6$=Cl in formula (II))
letrazuril ($R^4$=Cl, $R^5$=Cl, $R^6$=F in formula (II)) and
diclazuril ($R^4$=Cl, $R^5$=Cl, $R^6$=Cl in formula (II))).

The most preferred of these 1,2,4-triazinediones is diclazuril.

Particularly preferred as active ingredients according to the invention are the triazinetriones of the formula (I):

$R^2$ is preferably alkyl or alkoxy having in each case up to 4 carbon atoms, particularly preferably is methyl, ethyl, n-propyl, i-propyl.
$R^3$ is preferably perfluoroalkyl having 1 to 3 carbon atoms, and is particularly preferably trifluoromethyl or pentafluoroethyl.

Example of particularly preferred triazinetriones of the formula (I) are:
toltrazuril ($R^1$=$R^3$—S—, $R^2$=$CH_3$, $R^3$=$CF_3$)
ponazuril ($R^1$=$R^3$—$SO_2$—, $R^2$=$CH_3$, $R^3$=$CF_3$)
Of these, toltrazuril is most preferred.

It is possible with all the pharmaceutically active ingredients—as explained in detail above for the quinolones—to use the corresponding pharmaceutically acceptable salts, hydrates, solvates and where appropriate various modifications.

Optically active substances can be used in the form of their stereoisomers or as mixture of stereoisomers, e.g. as pure or enriched enantiomers or as racemates.

In the suspensions or medicaments of the invention it is possible for the active ingredients to be present singly in each case or to be employed in combination with further active ingredients.

In a preferred embodiment, the formulation of the invention can be adjusted so that it has thixotropic properties, meaning that it becomes less viscous on shaking, and the viscosity increases again at rest. This leads to satisfactory removability from the primary packaging, and to rapid reconstitution; this is advantageous for example on applications in the auditory canal, so that the applied formulation remains in the ear and cannot be ejected for example by shaking the head. Thixotropic formulations are produced by adding an appropriate additive to the formulation base (fluid, oily base) if the fluid base is not itself thixotropic. Such an additive is normally a suspension stabilizer or thickener such as, for example, colloidal silicon dioxides. The extent of the thixotropy can be specifically adjusted by varying the concentration.

The formulations may comprise further conventional pharmaceutically suitable additives and excipients. Examples which may be mentioned are
further thickeners are not usually necessary but may be employed where appropriate. Examples of further thickeners which may be mentioned are: cellulose derivatives such as methylcellulose, hydroxypropylcellulose, hydroxyethylcellulose, hydroxypropylmethylcellulose, carboxymethylcellulose, microcrystalline cellulose; bentonites, kaolin, pectin, starches, modified starch, waxes, agar, paraffins, gelatin, alginates, polyvinylpyrrolidone, crospovidone, cetyl alcohol, stearates such as, for example, magnesium stearate, zinc stearate or glyceryl stearate, saturated or unsaturated long-chain fatty acids ($C_8$-$C_{24}$, high molecular weight polyethylene glycols (e.g. polyethylene glycol 2000) and silicas.
Preservatives such as, for example, carboxylic acids (sorbic acid, propionic acid, benzoic acid, lactic acid), phenols (cresols, p-hydroxybenzoic esters such as methylparaben, propylparaben etc.), aliphatic alcohols (benzyl alcohol, ethanol, butanol etc.), quaternary ammonium compounds (benzalkonium chloride, cetylpyridinium chloride)
Antioxidants such as, for example, sulfites (Na sulfite, Na metabisulfite), organic sulfides (cystine, cysteine, cysteamine, methionine, thioglycerol, thioglycolic acid, thiolactic acid), phenols (tocopherols, as well as vitamin E and vitamin E DPGS (d-alpha-tocopheryl polyethylene glycol 1000 succinate)), butylated hydroxyanisole, butylated hydroxytoluene, gallic acid (propyl, octyl and dodecyl gallate), organic acids (ascorbic acid, citric acid, tartaric acid, lactic acid) and salts and esters thereof.

Wetting agents or emulsifiers such as, for example, fatty acid salts, fatty alkyl sulfates, fatty alkylsulfonates, linear alkylbenzenesulfonates, fatty alkyl polyethylene glycol ether sulfates, fatty alkyl polyethylene glycol ethers, alkylphenol polyethylene glycol ethers, alkyl polyglycosides, fatty acid N-methylglucamides, polysorbates, sorbitan fatty acid esters, lecithins and poloxamers.

Pharmaceutically acceptable colorants such as, for example, iron oxides, carotenoids, etc.

The formulations may also comprise cosolvents which reduce the viscosity. These are normally employed in proportions of 0.1 to 40% by weight, preferably of 1 to 10% by weight. Examples of cosolvents which may be mentioned are: pharmaceutically acceptable alcohols such as ethanol or benzyl alcohol, dimethyl sulfoxide, ethyl lactate, ethyl acetate, triacetin, N-methylpyrrolidone, glycerol formal, propylene carbonate, benzyl benzoate, glycofurol, dimethylacetamide, 2-pyrrolidone, isopropylideneglycerol, glycerol and polyethylene glycols. Mixtures of the aforementioned solvents can also be employed as cosolvents.

Water

Spreading agents which can be employed are inter alia hexyldodecanol, decyl oleate, dibutyl adipate, dimethicone, glyceryl ricinoleate, octyldodecanol, octyl stearate, propylene glycol dipelargonate and preferably isopropyl myristate or isopropyl palmitate.

Penetration enhancers (or permeation enhancers) improve the transdermal administration of medicaments and are known in principle in the state of the art (see, for example, chapter 6 of Dermatopharmazie, Wissenschaftliche Verlagsgesellschaft mbH Stuttgart, 2001). Examples which may be mentioned are spreading oils such as isopropyl myristate, dipropylene glycol pelargonate, silicone oils and their copolymers with polyethers, fatty acid esters (e.g. oleyl oleate), triglycerides, fatty alcohols, and linolene. DMSO, N-methylpyrrolidone, 2-pyrrolidone, dipropylene glycol monomethyl ether, octyldodecanol, oleyl macrogol glycerides or propylene glycol laurate can likewise be used.

The formulations are produced by the active ingredients or excipients which are to be dissolved or suspended being dispersed in the base. A homogenizer or high-pressure homogenizer is employed where appropriate for the dispersing. The sequence of addition of individual ingredients may be varied according to the formulation. After all the formulation ingredients have been dispersed, the finished formulation is put into interim storage or put directly into the primary packaging.

In principle, all possible primary packagings are suitable for the suspensions or medicaments of the invention. In a preferred embodiment, single-dose containers are used as primary packaging. These are charged with a volume of 0.1-0.5 ml, preferably 0.2-0.4 ml, particularly preferably 0.3-2.0 ml, as removable content of formulation.

The medicaments of the invention are generally suitable for use in humans and animals. They are preferably employed in animal management and animal breeding for productive and breeding livestock, zoo, laboratory, experimental and companion animals, especially for mammals.

The productive and breeding livestock include mammals such as, for example, cattle, horses, sheep, pigs, goats, camels, water buffaloes, donkeys, rabbits, fallow deer, reindeer, fur-bearing animals such as, for example, mink, chinchilla, raccoon, and birds such as, for example, chickens, geese, turkeys, ducks, pigeons and ostriches. Examples of preferred productive livestock are cattle, sheep, pigs and chickens.

The laboratory and experimental animals include dogs, cats, rabbits and rodents such as mice, rats, guinea pigs and golden hamsters.

Companion animals include dogs, cats, horses, rabbits, rodents such as golden hamsters, guinea pigs, mice, also reptiles, amphibians and birds for keeping at home and in zoos.

The medicaments of the invention are preferably employed for companion animals, specifically in particular for dogs and cats.

Both prophylactic and therapeutic use are possible.

The medicaments described herein are suitable in principle for all possible modes of administration such as, for example, dermal, oral, rectal, vaginal or nasal administration. They are particularly suitable for example for local administration into the auditory canals.

The described formulations are therefore particularly suitable for hygienic treatment of disorders of the auditory canal such as otitis externa in dogs and cats. For this purpose they are preferably put into single-dose containers as primary packaging. It should be particularly emphasized that the formulation can be removed very reproducibly. If thickeners are employed in suspension formulations it is usually possible to prevent sedimentation of the suspended ingredients. Thixotropic formulations are particularly advantageous because, after shaking the single-dose containers, the formulation can—even if the active ingredient concentrations are low—be removed particularly reproducibly, the formulation can, owing to the thixotropy and the single-dose container, be administered simply and hygienically into the animal ear and nevertheless cannot for example be ejected by the usual shaking of the head. It is likewise desirable that the formulation have good spreading behavior because the formulation is to be satisfactorily distributed in the auditory canal after administration.

Medicaments for administration in the auditory canal may preferably comprise antibiotics, corticoids or antimycotics as described hereinabove. A combination of antibiotics and corticoids is preferred, and a triple combination of antibiotics, corticoids and antimycotics is particularly preferred. The statements made above about preferred embodiments for the respective groups of active ingredients also apply to this area of use.

Examples of particularly preferred combinations of active ingredients which may be mentioned are: pradofloxacin, clotrimazole and dexamethasone (preferably in the form of its acetate), and enrofloxacin, bifonazole and dexamethasone (preferably in the form of its acetate).

DETERMINATION OF THE SEDIMENTATION KINETICS

FIG. 1 depicts the sedimentation kinetics of formulations with hydrophobic silica. The measurements were carried out with a so-called Lumifuge by measuring the diffraction of light. The sedimentation kinetics depict the sedimentation of the formulation on the y axis ("Interphase Height") and the duration of exposure to gravity in the centrifugal field on the x axis (indicated in hours). A formulation which has an interface height of 100% does not sediment under the applied gravity, and a formulation with an interface height of for example 80% sediments more than one with for example 90%.

The measured formulations, inter alia that of Example 13, comprise a hydrophobic silica (Aerosil R972, a methylated silica from Degussa) and toltrazuril in low-viscosity paraffin. The lowermost curve contains no addition of polyethoxylated compounds, and the other curves contain polyethoxylated compounds as addition, specifically poloxamer from BASF (Pluronic PE8100, Pluronic PE3100 and Pluronic RPE3110).

It is evident that the formulation with hydrophobic silica without addition of a polyethoxylated compound (poloxamer) shows the lowest curve profile. All the other formulations which, besides the hydrophobic silica, comprise addition of polyethoxylated compounds (various poloxamers as named above) lie distinctly higher. The sedimentation properties (i.e. the prevention of sedimentation) of the formulations with addition of polyethoxylated compounds are thus distinctly improved by comparison with the formulation without addition of polyethoxylated compounds.

EXAMPLES

The percentage data for the formulations described herein are indicated in weight per volume. Medium-chain triglycerides to be used are the triglycerides of caprylic/capric esters, for example Miglyol® 812 from Sasol/Witten (e.g. used in Examples 3 and 6). The methylated silica Aerosil® R972 from Degussa is used as colloidal hydrophobic silicas. (Aerosil R972 is a pyrogenic silica which is hydrophobized with dimethyldichlorosilane and is based on hydrophilic pyrogenic silica with a specific surface area of about 130 m$^2$/g and a degree of methylation of 66%-75%).

Example 1

0.14% pradofloxacin trihydrate
1.0% clotrimazole
0.05% dexamethasone acetate
4% benzyl alcohol
0.1% sorbic acid
0.05% polyoxyethylene 20 sorbitan monooleate
3.2% colloidal hydrophobic silica
ad 100% medium-chain triglycerides
0.1 g of sorbic acid is heated in 91 g of MCT to 60° C. and dissolved. At about 22°, 1.0 g of clotrimazole and 0.05 g of dexamethasone acetate are suspended. 0.14 g of pradofloxacin trihydrate are dissolved in 4 g of benzyl alcohol and mixed into the suspension. 0.05 g of polyoxyethylene 20 sorbitan monooleate and 3.2 g of colloidal hydrophobic silica are dispersed. The suspension is then homogenized for about 10 min with a homogenizer.

Example 2

0.14% pradofloxacin trihydrate
1.0% clotrimazole
0.05% dexamethasone acetate
0.1% sorbic acid
0.05% polyoxyethylene 20 sorbitan monooleate
3.2% colloidal hydrophobic silica
ad 100% medium-chain triglycerides
0.1 g of sorbic acid is heated in 95 g of MCT to 60° C. and dissolved. At about 22°, 0.14 g of pradofloxacin trihydrate, 1.0 g of clotrimazole, 0.05 g of dexamethasone acetate, 0.05 g of polyoxyethylene 20 sorbitan monooleate and 3.2 g of colloidal hydrophobic silica are dispersed. The suspension is then homogenized for about 10 min with a homogenizer.

Example 3

0.14% pradofloxacin trihydrate
1.0% clotrimazole
0.05% dexamethasone acetate
4% benzyl alcohol
0.1% sorbic acid
0.05% glycerol polyethylene glycol ricinoleate (prepared from 1 mol of castor oil and 35 ml of ethylene oxide. The product contains 83% hydrophobic polyoxyethylene glycerol ricinoleate compounds and about 17% hydrophilic polyoxyethylene glycerol and polyethylene glycol)
3.2% colloidal hydrophobic silica
ad 100% medium-chain triglycerides
0.1 g of sorbic acid is heated in 91 g of MCT to 60° C. and dissolved. At about 22°, 1.0 g of clotrimazole and 0.05 g of dexamethasone acetate are suspended. 0.14 g of pradofloxacin trihydrate are dissolved in 4 g of benzyl alcohol and mixed into the suspension. 0.05 g of polyoxyethylene 20 sorbitan monooleate and 3.2 g of colloidal hydrophobic silica are dispersed. The suspension is then homogenized for about 10 min with a homogenizer.

Example 4

0.14% pradofloxacin trihydrate
1.0% clotrimazole
0.05% dexamethasone acetate
0.1% sorbic acid
0.05% glycerol polyethylene glycol ricinoleate
3.2% colloidal hydrophobic silica
ad 100% medium-chain triglycerides
0.1 g of sorbic acid is heated in 95 g of MCT to 60° C. and dissolved. At about 22°, 0.14 g of pradofloxacin trihydrate, 1.0 g of clotrimazole, 0.05 g of dexamethasone acetate, 0.05 g of polyoxyethylene 20 sorbitan monooleate and 3.2 g of colloidal hydrophobic silica are dispersed. The suspension is then homogenized for about 10 min with a homogenizer.

Example 5

0.14% pradofloxacin trihydrate
1.0% bifonazole
0.05% dexamethasone acetate
4% benzyl alcohol
0.1% sorbic acid
0.05% polyoxyethylene 20 sorbitan monooleate
3.2% colloidal hydrophobic silica
ad 100% medium-chain triglycerides
0.1 g of sorbic acid is heated in 91 g of MCT to 60° C. and dissolved. At about 22°, 1.0 g of bifonazole and 0.05 g of dexamethasone acetate are suspended. 0.14 g of pradofloxacin trihydrate are dissolved in 4 g of benzyl alcohol and mixed into the suspension. 0.05 g of polyoxyethylene 20 sorbitan monooleate and 3.2 g of colloidal hydrophobic silica are dispersed. The suspension is then homogenized for about 10 min with a homogenizer.

Example 6

0.14% pradofloxacin trihydrate
1.0% bifonazole
0.05% dexamethasone acetate
0.1% sorbic acid 0.05% polyoxyethylene 20 sorbitan monooleate
3.2% colloidal hydrophobic silica
ad 100% medium-chain triglycerides
0.1 g of sorbic acid is heated in 95 g of MCT to 60° C. and dissolved. At about 22°, 0.14 g of pradofloxacin trihydrate, 1.0 g of bifonazole, 0.05 g of dexamethasone acetate, 0.05 g of polyoxyethylene 20 sorbitan monooleate and 3.2 g of colloidal hydrophobic silica are dispersed. The suspension is then homogenized for about 10 min with a homogenizer.

Example 7

0.1% enrofloxacin
1.0% clotrimazole
0.05% dexamethasone acetate
4% benzyl alcohol
0.1% sorbic acid
0.05% polyoxyethylene 20 sorbitan monooleate
3.2% colloidal hydrophobic silica
ad 100% medium-chain triglycerides
0.1 g of sorbic acid is heated in 91 g of MCT to 60° C. and dissolved. At about 22°, 1.0 g of clotrimazole and 0.05 g of dexamethasone acetate are suspended. 0.1 g of enrofloxacin are dissolved in 4 g of benzyl alcohol and mixed into the suspension. 0.05 g of polyoxyethylene 20 sorbitan monooleate and 3.2 g of colloidal hydrophobic silica are dispersed. The suspension is then homogenized for about 10 min with a homogenizer.

Example 8

0.1% enrofloxacin
1.0% clotrimazole
0.05% dexamethasone acetate
0.1% sorbic acid
0.05% polyoxyethylene 20 sorbitan monooleate
3.2% colloidal hydrophobic silica
ad 100% medium-chain triglycerides
0.1 g of sorbic acid is heated in 95 g of MCT to 60° C. and dissolved. At about 22°, 0.1 g of enrofloxacin, 1.0 g of clotrimazole, 0.05 g of dexamethasone acetate, 0.05 g of polyoxyethylene 20 sorbitan monooleate and 3.2 g of colloidal hydrophobic silica are dispersed. The suspension is then homogenized for about 10 min with a homogenizer.

Example 9

0.1% enrofloxacin
1.0% bifonazole
0.05% dexamethasone acetate
4% benzyl alcohol
0.1% sorbic acid
0.05% polyoxyethylene 20 sorbitan monooleate
3.2% colloidal hydrophobic silica
ad 100% medium-chain triglycerides
0.1 g of sorbic acid is heated in 91 g of MCT to 60° C. and dissolved. At about 22°, 1.0 g of bifonazole and 0.05 g of dexamethasone acetate are suspended. 0.1 g of enrofloxacin are dissolved in 4 g of benzyl alcohol and mixed into the suspension. 0.05 g of polyoxyethylene 20 sorbitan monooleate and 3.2 g of colloidal hydrophobic silica are dispersed. The suspension is then homogenized for about 10 min with a homogenizer.

Example 10

0.1% enrofloxacin
1.0% bifonazole
0.05% dexamethasone acetate
0.1% sorbic acid
0.05% polyoxyethylene 20 sorbitan monooleate
3.2% colloidal hydrophobic silica
ad 100% medium-chain triglycerides
0.1 g of sorbic acid is heated in 95 g of MCT to 60° C. and dissolved. At about 22°, 0.1 g of enrofloxacin, 1.0 g of bifonazole, 0.05 g of dexamethasone acetate, 0.05 g of polyoxyethylene 20 sorbitan monooleate and 3.2 g of colloidal hydrophobic silica are dispersed. The suspension is then homogenized for about 10 min with a homogenizer.

Example 11

0.1% enrofloxacin
1.0% bifonazole
0.05% triamcinolone acetate
4% benzyl alcohol
0.1% sorbic acid
0.05% polyoxyethylene 20 sorbitan monooleate
3.2% colloidal hydrophobic silica
ad 100% medium-chain triglycerides
0.1 g of sorbic acid is heated in 91 g of MCT to 60° C. and dissolved. At about 22°, 1.0 g of bifonazole and 0.05 g of triamcinolone acetate are suspended. 0.1 g of enrofloxacin are dissolved in 4 g of benzyl alcohol and mixed into the suspension. 0.05 g of polyoxyethylene 20 sorbitan monooleate and 3.2 g of colloidal hydrophobic silica are dispersed. The suspension is then homogenized for about 10 min with a homogenizer.

Example 12

0.1% enrofloxacin
1.0% bifonazole
0.05% triamcinolone acetate
0.1% sorbic acid
0.05% polyoxyethylene 20 sorbitan monooleate
3.2% colloidal hydrophobic silica
ad 100% medium-chain triglycerides
0.1 g of sorbic acid is heated in 95.5 g of MCT to 60° C. and dissolved. At about 22°, 0.1 g of enrofloxacin, 1.0 g of bifonazole, 0.05 g of triamcinolone acetate, 0.05 g of polyoxyethylene 20 sorbitan monooleate and 3.2 g of colloidal hydrophobic silica are dispersed. The suspension is then homogenized for about 10 min with a homogenizer.

Example 13

5% toltrazuril
0.07% poloxamer (Pluronic PE 3100)
3% colloidal hydrophobic silica
ad 100% paraffin, low-viscosity
5 g of toltrazuril, 0.07 g of poloxamer and 3 g of colloidal hydrophobic silica are dispersed in 92 g of paraffin. The suspension is then homogenized for about 10 min with a homogenizer.

The invention claimed is:

1. A method for stabilizing a fluid oil-based suspension comprising an active pharmaceutical ingredient and a hydrophobic silica against sedimentation, the method comprising contacting the hydrophobic silica with an amphiphilic substance comprising a nonionic polyoxyethylated compound in the fluid oil-based suspension, wherein the polyoxyethylated compound is selected from the group consisting of poloxamers, polyoxyethylene fatty acid glycerides, polyoxyethylene sorbitan fatty acid esters, polyoxyethylene fatty acids, and polyoxyethylene fatty alcohols, and wherein the stabilized fluid oil-based suspension, following contact with the amphiphilic substance, comprises the amphiphilic substance in a proportion of 0.001-0.15% by weight.

2. The method according to claim 1, wherein the active ingredient is a fluoroquinolone.

3. The method according to claim 2, wherein the fluoroquinolone is enrofloxacin.

4. The method according to claim 2, wherein the fluoroquinolone is pradofloxacin.

5. The method according to claim 2, wherein the fluoroquinolone is marbofloxacin.

6. The method according to claim 2, further comprising an antimycotic.

7. The method according to claim 6, wherein the antimycotic is selected from the group consisting of clotrimazole, miconazole and bifonazole.

8. The method according to claim 2, further comprising a corticoid.

9. The method according to claim 8, wherein the corticoid is selected from the group consisting of dexamethasone, betamethasone and triamcinolone.

10. The method according to claim 1, wherein the active ingredient is a triazine.

11. The method according to claim 1, wherein the fluid oil-based suspension comprises the hydrophobic silica in a proportion of 0.15-4.0% by weight.

12. The method according to claim 1, wherein the stabilized fluid oil-based suspension, following contact with the amphiphilic substance, comprises the amphiphilic substance in a proportion of 0.01-0.07% by weight.

13. The method according to claim 1, wherein the stabilized fluid oil-based suspension, following contact with the amphiphilic substance, comprises the amphiphilic substance in a proportion of 0.005-0.09% by weight.

14. The method according to claim 1, wherein the stabilized fluid oil-based suspension, following contact with the amphiphilic substance, comprises the amphiphilic substance in a proportion of 0.005-0.08% by weight.

* * * * *